United States Patent
Grafmans et al.

(10) Patent No.: US 8,338,644 B2
(45) Date of Patent: *Dec. 25, 2012

(54) METHOD FOR THE PRODUCTION OF N,N-DIMETHYLACETAMIDE (DMAC)

(75) Inventors: Horst Grafmans, Bad Duerkheim (DE); Steffen Maas, Bubenheim (DE); Alexander Weck, Freinsheim (DE); Heinz Ruetter, Kapellen (BE); Michael Schulz, Worms (DE); Karl-Heinz Ross, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/967,798

(22) Filed: Dec. 14, 2010

(65) Prior Publication Data
US 2011/0082316 A1    Apr. 7, 2011

Related U.S. Application Data

(63) Continuation of application No. 11/720,774, filed as application No. PCT/EP2005/012982 on Dec. 3, 2005, now abandoned.

(30) Foreign Application Priority Data

Dec. 6, 2004 (DE) .......... 10 2004 058 886

(51) Int. Cl.
*C07C 231/02* (2006.01)
(52) U.S. Cl. ........................ 564/134
(58) Field of Classification Search .......... 564/134
See application file for complete search history.

(56) References Cited

U.S. PATENT DOCUMENTS

| 3,300,531 A | 1/1967 | James et al. |
| 3,538,159 A * | 11/1970 | Duffy ............................ 564/137 |
| 4,189,566 A | 2/1980 | Mueller et al. |
| 4,258,200 A | 3/1981 | Daughenbaugh |
| 6,037,381 A | 3/2000 | Beer et al. |
| 6,300,467 B1 | 10/2001 | Auer et al. |
| 2006/0219545 A1 | 10/2006 | Peschel et al. |

FOREIGN PATENT DOCUMENTS

| CA | 1073467 | 3/1980 |
| CA | 1073468 | 3/1980 |
| DE | 19758296 A1 | 7/1999 |
| DE | 19817113 A1 | 10/1999 |
| DE | 10315214 A1 | 10/2004 |
| EP | 0003112 A1 | 7/1979 |
| FR | 1406279 | 7/1965 |
| JP | 02160749 | 6/1990 |
| JP | 11092434 | 4/1999 |
| SU | 1004357 | 3/1983 |
| WO | WO-2006/000392 A1 | 1/2006 |
| WO | WO-2006/061153 A1 | 6/2006 |
| WO | WO-2006/061157 A1 | 6/2006 |

OTHER PUBLICATIONS

Faming Zhuanli Shenqing Gongkai Shuomingshu, 1663944, Sep. 7, 2005(Reaction only).*
"Organikum", VEB Deutscher Verlag der Wissenschaften, 1963, pp. 374-375.
Guthrie, J. P., "Hydration of Carboxamides. Evaluation of the Free Energy Change for Addition of Water to Acetamide and Formamide Derivatives", J. Am. Soc., 1974, vol. 96, pp. 3608-36015.

* cited by examiner

*Primary Examiner* — Shailendra Kumar
(74) *Attorney, Agent, or Firm* — Connolly Bove Lodge & Hutz LLP

(57) ABSTRACT

A process for preparing N,N-dimethylacetamide (DMAC) by continuously reacting methyl acetate (MeOAc) with dimethylamine (DMA) in the presence of a basic catalyst, wherein MeOAc is used in the form of a methanolic solution which is obtained as a by-product in the preparation of polyTHF by transesterifying polyTHF diacetate with methanol.

21 Claims, No Drawings

METHOD FOR THE PRODUCTION OF N,N-DIMETHYLACETAMIDE (DMAC)

RELATED APPLICATIONS

This application is a continuation application of U.S. patent application Ser. No. 11/720,774, filed Jun. 4, 2007, now abandonded, which is a national stage application (under 35 U.S.C. §371) of PCT/EP2005/012982, filed Dec. 3, 2005, which claims benefit of German Application No. 10 2004 058 886.4, filed Dec. 6, 2004.

The present invention relates to a process for preparing N,N-dimethylacetamide (DMAC) by continuously reacting methyl acetate (MeOAc) with dimethylamine (DMA) in the presence of a basic catalyst.

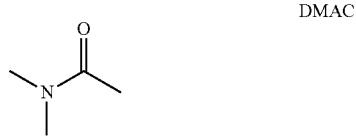

DMAC

DMAC finds use as a polar solvent, for example for polymers and for gases, as paint removers, extractants, catalysts and crystallization assistants. In the coatings industry, DMAC is used, owing to its high boiling point, for specific coating materials based on polymeric binders, for example polyamides and polyurethanes, DMAC is also used for producing fibers and films and as a reaction medium. In the spinning of Spandex® fibers, DMAC is used as an assistant and subsequently recovered at least partly.

DMAC may be prepared from acetic acid and dimethylamine, for example according to FR-A-1,406,279.

Carboxamides are also obtainable by aminolysis of corresponding carboxylic esters; cf., for example, 'Organikum', VEB Deutscher Verlag der Wissenschaften, 1963, pages 374-375.

The article by J. P. Guthrie in J. Am. Chem. Soc. 96, pages 3608-15 (1974) relates to reaction kinetics and thermodynamics aspects of reactions including the aminolysis of carboxylic esters.

CA-A-1 073 467 and CA-A-1 073 468 (both General Electric Comp.) describe the preparation of diols and N,N-dialkylamides by reacting carboxylic diol esters with dialkylamines.

U.S. Pat. No. 4,258,200 (Air Products) teaches the preparation of DMAC from methyl acetate and DMA in the presence of cobalt catalysts.

In Example 1, a "20% methanol-methyl acetate azeotrope" is used for the reaction at 155-160° F. (68.4-71.2° C.).

JP-A-02 160749 (Lion Akzo KK) relates, according to the Patent Abstracts of Japan, to the reaction of aliphatic carboxylic esters with ammonia or an amine, such as monomethylamine, ethylenediamine, diethylenetriamine, in the presence of an "alkali catalyst" at from 50 to 180° C., in particular from 80 to 160° C., and in the pressure range from standard pressure to 9.81 bar (10 kg·cm$^{-2}$·G).

From 0.1 to 10 mol %, in particular from 1 to 5 mot %, based on the carboxylic ester used, of sodium methoxide (NaOMe) is used as the catalyst.

Derwent Abstract 84-016399/03 (SU-A-1 004 357; Dnepr Chem. Techn. Inst.) describes the preparation of DMAC or dimethylformamide (DMF) by reacting a 5-20% excess of corresponding methyl carboxytate in methanol with DMA at 50-150° C. and subsequently recycling unreacted ester and methanol into the reaction stage.

In the example, a solution of 0.4 kg of methyl formate in 0.2 kg of methanol/h is reacted continuously with 0.2 kg of vaporous DMA/h to give DMF.

The two German patent applications No. 102004030616.8 of Jul. 24, 2004 and DE-A-10 315 214 to BASF AG relate to processes for purifying DMAC.

It is an object of the present invention to provide an improved, economically viable, selective, energy-saving and non-resource-intensive process for preparing N,N-dimethylacetamide (DMAC). The process should afford DMAC in high yield and space-time yield and in high purity (for example free or virtually free of acetic acid, high color quality).

Accordingly, a process has been found for preparing N,N-dimethylacetamide (DMAC) by continuously reacting methyl acetate (MeOAc) with dimethylamine (DMA) in the presence of a basic catalyst, which comprises using MeOAc in the form of a methanolic solution which is obtained as a by-product in the preparation of polyTHF by transesterifying polyTHF diacetate with methanol.

The process according to the invention can be performed as follows:

For DMAC synthesis, dimethylamine (DMA) is reacted continuously with a methanolic solution of methyl acetate (MeOAc), a secondary stream of polyTHF preparation.

Preference is given to using in the range from 0.2 to 2.0 mol, particularly from 0.5 to 1.5 mol, very particularly from 0.8 to 1.2 mol, for example from 0.9 to 1.1 mol or from 1.0 to 1.05 mol, of dimethylamine (DMA) per mole of methyl acetate.

The DMA used preferably has a purity of $\geq$99% by weight, in particular $\geq$99.4% by weight, and is, for example, in the range from 99.5 to 99.8% by weight.

The methanolic MeOAc solution preferably has a concentration in the range from 65 to 90% by weight, preferably from 70 to 85% by weight, in particular from 75 to 82% by weight, of MeOAc.

In a particular embodiment of the invention, the methanolic MeOAc solution used is a corresponding by-product stream which is obtained in the production of polyTHF (polytetrahydrofuran), for example by the two-stage BASF process according to EP-A-3112, DE-A-197 58 296 and/or DE-A-198 17 113.

The methanolic MeOAc solution is obtained as a corresponding by-product stream in the distillative workup, for example, in the form of a methyl acetate/methanol azeotrope (boiling point: 54° C./1013 mbar), since stoichiometric amounts of MeOAc are formed in the transesterification of polyTHF diacetate (=poly-(1,4-butanediol) bis(acetate)) with methanol to give polyTHF.

The methanolic MeOAc solution preferably has the following contents:
MeOAc: from 65 to 90% by weight, preferably from 70 to 85% by weight, in particular from 75 to 82% by weight,
Methanol: from 10 to 30% by weight, preferably from 14.8 to 25% by weight, in particular from 17.6 to 22% by weight,
Dimethyl ether: from 0 to 2% by weight, preferably from 0.1 to 1.5% by weight, in particular from 0.2 to 1.2% by weight,
THF: from 0 to 4% by weight, preferably from 0.1 to 3.5% by weight, in particular from 0.2 to 1.5% by weight, and
$H_2O$: from 0 to 0.1% by weight, preferably from 0 to 0.01% by weight, in particular from 0 to 0.003% by weight.

In particular, the methanolic MeOAc solution consists of MeOAc, MeOH, dimethyl ether, THF and water in the above-specified amounts.

The continuous reaction is preferably carried out at an absolute pressure in the range from 1 to 200 bar, preferably from 3 to 100 bar, in particular from 10 to 30 bar, very particularly from 12 to 25 bar, for example from 15 to 20 bar.

The reaction temperature is preferably in the range from 20 to 200° C., preferably from 60 to 140° C., in particular from 80 to 120° C., very particularly from 90 to 110° C., for example from 95 to 105° C.

Useful reactors for the inventive reaction are in particular backmixed reactors, for example stirred tank reactors or jet loop reactors, nonbackmixed reactors such as stirred tank batteries or tubular reactors, and special designs such as reaction columns with and without internal or external delay volumes, in which internal and external heat removal is possible.

The reaction is effected with particular preference in a jet loop reactor. The jet loop reactor is preferably equipped with an insert tube and nozzle at the bottom. Preference is given to adding DMA together with the catalyst through the circulation-pumped driving jet and the MeOAc through the outer jet.

To complete the conversion, particular preference is given to attaching downstream of the main reactor, for example the jet loop reactor, a postreactor, for example a flow tube or a cascaded delay vessel.

The reactor types mentioned are known to those skilled in the art, for example, from Ullmanns Enzyklopädie der Technischen Chemie, 4th edition, volume 13, p. 135 ff., and P. N. Rylander, "Hydrogenation and Dehydrogenation" in Ullmann's Encyclopedia of Industrial Chemistry, 5th ed. on CD-ROM.

In the process according to the invention, the basic catalyst used is preferably an alkali metal hydroxide, alkaline earth metal hydroxide, alkali metal alkoxide, alkaline earth metal alkoxide, alkali metal carbonate, alkaline earth metal carbonate, alkali metal hydrogencarbonate, alkaline earth metal hydrogencarbonate and/or an amine, in particular tertiary amine.

The alkali metal is Li, Na, K, Rb or Cs, in particular Na or K.

The alkaline earth metal is Be, Mg, Ca, Sr or Ba, in particular Mg or Ca.

The alkoxide is preferably a $C_{1-4}$-alkoxide, in particular methoxide.

The amine, especially an aliphatic amine, is preferably a $C_{3-12}$-alkylamine, for example triethylamine, tri-n-propylamine, tri-n-butylamine, dimethylethylamine, diethylmethylamine, N-methylpiperidine, triethylenediamine (TEDA).

In the process according to the invention, no cobalt catalysts according to U.S. Pat. No. 4,258,200 are used.

A very particularly preferred catalyst in the process according to the invention is sodium methoxide (NaOMe).

The catalyst is present in the reaction mixture in homogeneous and/or suspended form.

In the continuous process, preference is given to using in the range from 0.0002 to 0.09 mol, preferably from 0.002 to 0.05 mot, in particular from 0.003 to 0.02 mol, of the catalyst or catalyst mixture per mole of methyl acetate used.

The catalyst or the catalyst mixture is advantageously used in the form of a solution and/or suspension in a solvent or suspension medium.

Preferred solvents and/or suspension media are water and alcohols (e.g. $C_{1-4}$-alcohols such as methanol, ethanol, n-propanol, n-butanol) or mixtures thereof.

In the case of an alkali metal alkoxide as the catalyst, preference is given to dissolving the alkali metal alkoxide in the alcohol which corresponds to the alkoxide by protonation.

The catalyst or the catalyst mixture is used in the above-mentioned preferred amounts, preferably in the form of from 1 to 35% by weight, in particular from 5 to 30% by weight, solution or suspension.

Particularly advantageously, the catalyst used is NaOMe in the above-mentioned preferred amounts in the form of a methanolic solution, in particular in the form of a from 1 to 35% by weight solution, very particularly in the form of a from 25 to 30% by weight solution.

The reaction of the MeOAc in the process according to the invention is preferably carried out in the presence of less than 1% by weight, particularly less than 0.5% by weight, very particularly in the range from 0 to 0.3% by weight, of water, based in each case on the weight of the two feedstocks, MeOAc and DMA (in total).

The heat of reaction is removed preferably via an external heat exchanger. Particularly advantageously, the steam raised in the external heat exchanger, for example 1.5 bar steam, is utilized in a synthesis plant for methylamines from methanol and ammonia.

In the process according to the invention, the liquid reactor effluent from the synthesis stage consists of
in the range from 45 to 74.5% by weight, particularly from 50 to 70% by weight, of DMAC,
in the range from 25 to 45% by weight, particularly from 29 to 40% by weight, of methanol and
a total of from 0.5 to 6% by weight, particularly from 1 to 5% by weight, of DMA, methyl acetate, catalyst (for example sodium methoxide), if appropriate catalyst solvent/suspension medium and by-products.

As the result of the use of methanolic MeOAc solution which is obtained in the production of polyTHF, tetrahydrofuran (THF) and/or dimethyl ether may be such by-products.

For further workup, the liquid reactor effluent may be decompressed directly into a boiler of a distillation column.

In a particular embodiment, decompression is effected into two alternately operated distillation boilers.

Advantageously, water or an aqueous or anhydrous protic acid such as sulfuric acid, methanesulfonic acid, carboxylic acid (e.g. $C_{1-4}$-carboxylic acid), in particular phosphoric acid, is added to the effluent, preferably in an amount which ensures full conversion of the basic catalyst used to the corresponding acid and to the corresponding alkali metal, alkaline earth metal or ammonium salt of the protic acid. In other words, preference is given to fully neutralizing the basic catalyst used and present in the reactor effluent by reacting with $H^+$.

This is advantageous since the basic catalyst, for example sodium methoxide, would catalyze the dissociation of DMAC after the outgassing of residual DMA.

The organic product mixture is preferably removed from salts present by evaporation (at standard pressure or under reduced pressure, for example in a reboiler), for example until a salt which precipitates out distinctly reduces the heat exchanger output and leads to encrustations.

The boiler for the reactor effluent is then preferably changed and the residue of the old boiler is concentrated as far as possible by evaporation. The precipitated solid salt residue may be dissolved in water and disposed of as a solution in a water treatment plant.

The reactor effluent which has been evaporated off from the solid and partially or totally condensed is worked up by distillation, for example in one, two, three, four or more columns which are connected to one another if appropriate.

Preference is given to effecting the workup in three continuous distillation columns.

In one column A, methanol and any other low boilers (DMA, water, THF, methyl acetate, inter alia) are removed overhead at preferably from 0.8 to 1.2 bar.

In the distillation column D, preferably connected downstream, for low boiler purification, an aqueous or anhydrous methanol stream which may comprise DMA is enriched and is, for example, advantageously recycled for use in a methylamine synthesis plant (in particular for DMA preparation).

The bottom effluent of column A is fed to a column B. At preferably 100-500 mbar abs., pure DMAC ($\geq$99.5% by weight, in particular $\geq$99.7% by weight, very particularly $\geq$99.8% by weight, for example in the range from $\geq$99.9 to 99.99% by weight) is removed here, preferably via a liquid side draw which is disposed preferably in the rectifying section.

The top effluent of column B, comprising DMAC (e.g. 98% by weight of DMAC, in particular from 98.5 to 99.5% by weight of DMAC), is preferably recycled into column A.

The bottom effluent of column B is separated once more in a column C, preferably at standard pressure, and the top effluent comprising DMAC and methanol (e.g. approx. 94% by weight of DMAC and approx. 6% by weight of methanol) is preferably likewise recycled to column A and the bottom effluent of column C (high boilers, DMAC and added methanol) passes to disposal, for example incineration. The third column C distinctly reduces the amount of residue.

The distillative purification of DMAC may also be effected according to one of the processes of the two German patent applications 102004030616.8 of Jul. 24, 2004 and DE-A-10 315 214 (both BASF AG).

It has been recognized in accordance with the invention that the process may advantageously also be carried out in a plant which has originally been designed for the preparation of N,N-dimethylformamide (DMF) from carbon monoxide (CO) and DMA.

Slight modifications/plant improvements (for example postreactor, tank for DMAC and/or relating to the column connection) thus advantageously allows both DMF and DMAC, for example in alternating operation, to be prepared in the DMF plant as described, for example, in K. Weissermel, H.-J. Arpe, Industrielle Organische Chemie, Wiley-VCH, 5th edition 1998, page 49, or in general and in principle in JP-A2-110 92 434. In other words, the invention also enables the alternative or alternating production of DMAC in a DMF plant.

It is possible by the process according to the invention to achieve DMAC yields in the range of $\geq$88%, in particular $\geq$95%, very particularly $\geq$99%, for example from 99.5 to 99.9% (based in each case on MeOAc used), at MeOAc conversions in the range of $\geq$90%, in particular very particularly $\geq$99%, for example from 99.5 to 100%.

The DMAC space-time yields are in the range from 0.1 to 0.85 kg of DMAC/(liter of reactor volume·h), for example from 0.2 to 0.5 kg of DMAC/(liter of reactor volume·h).

The process according to the invention affords DMAC with a purity of $\geq$99.5% by weight, in particular $\geq$99.7% by weight, very particularly $\geq$99.8% by weight, for example in the range from $\geq$99.9 to $\geq$99.99% by weight (see below for method and conditions for purity determination), a water content $\leq$200 ppm, for example in the range from 50 to 150 ppm (to DIN 51777), and a Pt/Co color number $\leq$10, particularly $\leq$8, for example in the range from 1 to 6 (to DIN ISO 6271).

The acid content (calculated as acetic acid) of the DMAC is in particular $\leq$80 ppm, very particularly $\leq$70 ppm, for example in the range from 5 to 60 ppm (to DIN 53402).

All ppm data in this document relate to the weight (ppm by weight).

EXAMPLES

Example 1

For the one-stage DMAC, synthesis, 45.0 g/h of dimethylamine (DMA) were reacted at 20 bar and 120° C. with 95.5 g/h of methanolic methyl acetate (77.5% by weight) which had been obtained beforehand as a by-product stream in the production of polyTHF according to EP-A-3112, DE-A-197 58 296 and/or DE-A-198 17 113 (THF content 1.5% by weight). The water content in the feed (DMA+methanolic methyl acetate) was 109 ppm.

The reaction was effected in a loop reactor with a mean residence time (MRT) of 1 h and sodium methoxide (0.48 g/h) in methanolic solution (30% by weight) as the homogeneous catalyst. The heat was removed via an external heat exchanger. The energy removed in the external heat exchanger can raise 1.5 bar steam.

The liquid effluent from the synthesis stage consisted of 57.7% by weight of DMAC, 34.2% by weight of methanol, 5.0% by weight of methyl acetate and a total of 3.1% by weight of DMA, tetrahydrofuran, sodium methoxide and by-products.

Example 2

All settings from Example 1 were adopted. However, the water content of the feed stream was 550 ppm. After a short time, there were blockages in the reactor as a result of precipitated sodium acetate, and the experiment had to be stopped.

Example 3

For the two-stage DMAC synthesis, 45.2 g/h of dimethylamine (DMA) were reacted with 92.5 g/h of methanolic methyl acetate (78.8% by weight) which had been obtained beforehand as a by-product stream in the production of polyTHF according to EP-A-3112, DE-A-197 58 296 and/or DE-A-198 17 113 (THF content: 1.0% by weight), at 20 bar and 120° C.

The reaction was effected in a loop reactor with a mean MRT of 1 h and sodium methoxide (0.56 g/h) in methanolic solution (30% by weight) as the homogeneous catalyst. The heat was removed via an external heat exchanger. The energy removed in the external heat exchanger can generate 1.5 bar steam.

The liquid effluent from the synthesis stage consisted of 53.9% by weight of DMAC, 36.3% by weight of methanol, 3.9% by weight of methyl acetate and a total of 5.9% by weight of DMA, tetrahydrofuran, sodium methoxide and by-products.

This effluent was conveyed in straight pass through a tubular reactor at 120° C., 20 bar and a mean MRT of 1 h. The effluent consisted of 58.3% by weight of DMAC, 37.3% by weight of methanol, 1.1% by weight of methyl acetate and a total of 3.3% by weight of DMA, tetrahydrofuran, sodium methoxide and by-products.

Example 4

10% by weight of $H_2O$, a superstoichiometric amount relative to the catalyst, was added continuously to a reaction effluent according to Example 3 in order to replace the sodium methoxide. In a continuous evaporation still, all volatile constituents (1.8 kg/h) were distilled off at 135° C. The salt residue (245 g) which had been collected within 20 operating hours and had been concentrated to dryness in the bottom of the still was dissolved in 1.5 kg of $H_2O$ and removed without residue from the still into wastewater in need of treatment.

Example 5

A reaction effluent according to Example 3 was admixed continuously with 85% phosphoric acid for the stoichiometric formation of $Na_2HPO_4$. On completion of catalyst decomposition and evaporation of the volatile constituents according to Example 4, 400 g/h of the condensed mixture were fed continuously to a distillation column, and a high boiler stream (218 g/h) comprising 99.2% by weight of DMAC and 0.8% by weight of by-products was drawn off at a bottom temperature of 175° C. In a subsequent continuous distillation, this stream was worked up further, and 198 g/h of DMAC with a purity of 99.9% were obtained from a side draw.

What is claimed is:

1. A process for preparing N,N-dimethylacetamide (DMAC) comprising the step of continuously reacting methyl acetate (MeOAc) with dimethylamine (DMA) in the presence of a basic catalyst, wherein said MeOAc is in the form of a methanolic solution obtained as a by-product in the preparation of polyTHF via transesterification of polyTHF diacetate with methanol.

2. The process according to claim 1, wherein said reaction is carried out at a temperature in the range from 80 to 140° C.

3. The process according to claim 1, wherein said reaction is carried out at an absolute pressure in the range from 3 to 30 bar.

4. The process according to claim 1, wherein said methanolic MeOAc solution comprises from 70 to 85% by weight of MeOAc, from 14.8 to 25% by weight of methanol, from 0.1 to 1.5% by weight of dimethyl ether, from 0.1 to 3.5% by weight of tetrahydrofuran (THF), and from 0 to 0.01% by weight of water.

5. The process according to claim 1, wherein said methanolic MeOAc solution comprises from 75 to 82% by weight of MeOAc, from 17.6 to 22% by weight of methanol, from 0.2 to 1.2% by weight of dimethyl ether, from 0.2 to 1.5% by weight of THF, and from 0 to 0.003% by weight of water.

6. The process according to claim 1, wherein said catalyst is sodium methoxide.

7. The process according to claim 6, wherein said catalyst is in the form of a methanolic solution.

8. The process according to claim 1, wherein said catalyst is present in the range of from 0.0002 to 0.09 mole per mole of MeOAc.

9. The process according to claim 1, wherein said reaction is carried out in a jet loop reactor.

10. The process according to claim 9, wherein said jet loop reactor comprises an insert tube and a nozzle located at the bottom of said jet loop reactor.

11. The process according to claim 1, comprising the additional step of neutralizing said catalyst present in the reactor effluent after the reaction and before distillative workup by reacting said catalyst with a protic acid or by decomposing said catalyst with water.

12. The process according to claim 11, wherein said protic acid is phosphoric acid.

13. The process according to claim 11, comprising the additional step of removing the organic product mixture after neutralization with a protic acid and before distillative workup by evaporating said organic product mixture from salts present after the reaction.

14. The process according to claim 1, comprising the additional step of continuously distillatively working-up reaction effluent in a column A, wherein methanol and any other low boilers are initially removed overhead in column A, followed by feeding the bottom effluent of column A to a column B, wherein DMAC is removed via a side draw, and wherein said DMAC has a purity of greater than or equal to 99.7% by weight.

15. The process according to claim 14, wherein said DMAC is removed in column B via a liquid side draw which is disposed in the rectifying section of column B.

16. The process according to claim 14, wherein the top effluent of column B comprises DMAC and is recycled back into column A.

17. The process according claim 14, wherein the bottom effluent of column B is separated into a column C, wherein the top effluent of column B is recycled into column A, and wherein said top effluent comprises DMAC and methanol.

18. The process according to claim 14, wherein the top effluent of column A comprises methanol and is purified in a column D.

19. The process according to claim 1, wherein the DMAC prepared has a purity of greater than or equal to 99.7% by weight, a water content of less than or equal to 200 ppm, and a Pt/Co color number less than or equal to 10.

20. The process according to claim 1, wherein the DMAC prepared has an acid content calculated as acetic acid of less than or equal to 80 ppm.

21. The process according to claim 1, wherein said process is carried out in a plant wherein DMF can also be prepared from carbon monoxide and DMA.

* * * * *